United States Patent [19]

DeYoung

[11] Patent Number: 4,554,164
[45] Date of Patent: Nov. 19, 1985

[54] PARENTERAL FORMULATION

[75] Inventor: Joyce L. DeYoung, Wayne, Pa.

[73] Assignee: American Home Products Corporation, New York, N.Y.

[21] Appl. No.: 656,062

[22] Filed: Sep. 28, 1984

[51] Int. Cl.[4] ........................................... A61K 31/135
[52] U.S. Cl. .................................................... 514/649
[58] Field of Search ......................................... 424/330

[56] References Cited

PUBLICATIONS

Remington's Pharmaceutical Sciences, 16th Ed., (1980), pp. 238–239, 1225–1226, 1256.
Staquet, Curr. Med. Res. Opin., 6, 475–477, (1980).
Chan et al., Analytica Chimica Acta., 105, 423–428, (1979).

Primary Examiner—Stanley J. Friedman
Attorney, Agent, or Firm—Richard K. Jackson

[57] ABSTRACT

Improved parenteral formulations of 1-cis-2($\alpha$-dimethylamino-m-hydroxybenzyl)cyclohexanol containing from about 20 to about 40 percent propylene glycol (USP).

5 Claims, No Drawings

PARENTERAL FORMULATION

BACKGROUND OF THE INVENTION

Ciramadol is a potent analgesic possessing a mixed agonist-antagonist activity profile upon either oral or parenteral administration [Staquet, Curr. Med. Res. Opin., 6, 475 (1980)]. Ciramadol is known to undergo photolytic decomposition [Chan et al., Anal. Chim. Acta, 105, 423 (1979)]. Human clinical trials by parenteral administration have heretofore been conducted using a lyophilized product reconstituted with saline for injection. No problem of insolubles formation has been observed with these formulations.

DESCRIPTION OF THE INVENTION

It has now been discovered that ready made injectable saline solutions containing typically 6.0 percent weight per volume of Ciramadol, about 0.9 percent weight per volume NaCl (USP) and water for injection (USP) to make 1.0 ml., which are chemically stable, develop insolubles as early as six months when stored at room temperature. At elevated temperatures (45° C.) and Ciramadol concentrations of 1.0, 2.0 and 3.0 percent weight per volume in saline, insolubles were observed in about three months. An attendant rise in pH of approximately one pH unit (from about 5.4 to 6.4) also was observed after four months storage in Tubex ® sterile cartridge units. No pH change has been observed in ampules stored under the same condition of elevated temperature. The insoluble material appeared in each case as a fine, white, amorphous material in very small amounts, usually observable only with a light box to aid viewing or by magnification. The minute quantities of insoluble material were insufficient in amount for qualitative analysis beyond identification as organic in nature. No significant loss in therapeutic level of drug activity attended the formation of these insolubles.

Because it is most desirable to provide ready made injectables with a room temperature shelf life of approximately two years (the accelerated shelf life study at 45° C. for three months mentioned in the preceding paragraph represents an approximate equivalent of one year at room temperature) an improved injectable formulation for parenteral administration is needed.

Thus, in accordance with this invention there is provided a stable, parenteral, aqueous solution of a therapeutically effective amount of a pharmaceutically acceptable acid addition salt of Ciramadol [1-cis-2($\alpha$-dimethylamino-m-hydroxybenzyl)cyclohexanol] in unit dosage form which comprises from about 10 to about 100 milligrams of said acid addition salt of 1-cis-2($\alpha$-dimethylamino-m-hydroxybenzyl)-cyclohexanol; from 0.05 to about 0.5 percent of an antioxidant selected from the group consisting of monothioglycerol (NF), sodium bisulfite, sodium bisulfite and disodium ethylenediamine-tetraacetic acid, and disodium ethylenediaminetetraacetic acid and monothioglycerol (NF); optionally from about 0.005 to about 0.01 percent of a preservative such as benzethonium chloride; from 0.5 to about 2.0 percent of a buffer selected from the group consisting of a lactate, tartrate, citrate and acetate buffer systems at a pH of from about pH 3 to about pH 4.5; and from about 20 to about 40 percent propylene glycol (USP); per milliliter of water for injection. The concentrations expressed here and throughout this disclosure are on a weight/volume basis.

Preferred formulations for parenteral administration contain per milliliter water for injection, from about 1.0 to about 6.0 percent weight per volume Ciramadol HCl; about 0.1 to about 0.5 percent weight per volume monothioglycerol (NF); about 0.5 to about 1.0 percent weight per volume lactic acid (USP); about 20 to about 40 percent weight per volume propylene glycol (USP); and enough sodium hydroxide to produce a pH of from about 4 to about 4.5.

The formulations of this invention are self-preserving [as established by the technique published in U.S. Pharmacopeia XX, pp. 873–874, (1980)] and need no additive preservative ingredient. Three month light exposure studies (200 foot candles, fluorescent light) demonstrate no observable chemical or physical changes. All storage stability studies in various size ampules, Tubex ®, and vials, filled and half-filled, have indicated stable solutions throughout the drug concentration range for at least twenty-four months at room temperature. Thus, the formulations of this invention provide clear solutions of Ciramadol suitable for parenteral injection. These new formulations are stable in storge for at least two years and provide a dosage form which may be maintained in ready-to-use form thereby avoiding separate packaging of diluent and drug and the necessity for reconstitution at the time of administration.

Although propylene glycol has been used heretofore as a nonaqueous solvent for the purpose of improving aqueous solubility of active drug substances and is classified as a nonaqueous solvent, it is not employed for that purpose in the formulations of this invention. Ciramadol, in the form of its acid addition salts, is very soluble in water (greater than 500 mg/ml $H_2O$) and needs no additional solvent. For purposes of this invention, propylene glycol has been found to prevent the formation of unknown trace insolubles which develop in completely aqueous formulations containing Ciramadol acid addition salts.

The parenteral formulations of this invention are readily prepared by simple admixing of the individual components in any order desired.

Specifically preferred formulations of this invention contain 1.5, 3.0 or 6.0 percent weight per volume of Ciramadol and are constituted as follows:

| | |
|---|---|
| Ciramadol.HCl | 1.5, 3.0 or 6.0 percent |
| Monothioglycerol (NF) | 0.5 percent |
| Lactic acid (USP) | 0.9 percent |
| Sodium Hydroxide, 3N | q.s. to pH 4.0 |
| Propylene glycol (USP) | 21 percent |
| Water for injection (USP) | q.s. ad. 1.0 milliliter |

The following formulations for parenteral administration of Ciramadol illustrate additional unsuccessful attempts to prevent the formation of insoluble material in ready-made unit dosage forms as well as stable formulations of this invention. Table I presents formulations in addition to the simple saline solutions and aqueous solutions referred to supra, which do not avoid the problem of insolubles formation and Table II presents formulations which do avoid the problem. The acceptability or unacceptability of a given formulation was determined by filling the experimental formulations into packages (ampules, vials, Tubex ®, etc.) of the type and sizes conventionally used with parenteral drugs. These packages were stored at temperatures from 5° C. to 60° C. At various times, samples were examined for color change (any color easily seen in normal laboratory lighting) and development of insoluble material. The pH was measured and chemical assays performed to ascertain whether significant chemical loss had occurred and to assure maintenance of potency. If a sample developed insolubles at any time during its projected shelf-life (two years at room temperature) it was considered unsuitable. Because problems are more likely to occur at higher concentrations, the formulations presented in the following tables all represent studies at 6.0 weight percent per volume Ciramadol. All of the formulations in Table I developed insoluble material at one or more of the previously mentioned time-temperature points. In addition, many of them discolored. None of these problems occurred for two years at room temperature in the formulations presented in Table II where propylene glycol was present.

dimethylamino-m-hydroxybenzyl)cyclohexanol hydrochloride, about 0.1 to about 0.5 percent weight/volume monothioglycerol (NF), about 0.5 to about 1.0 percent weight/volume lactic acid (USP), about 20 to about 40 percent weight/volume propylene glycol (USP) and enough sodium hydroxide to produce a pH of from about 4 to about 4.5.

3. A composition of claim 1 which comprises about 1.5 percent weight/volume 1-cis-2(α-dimethylamino-m-hydroxybenzyl)cyclohexanol·HCl, about 0.5 percent weight/volume monothioglycerol, about 0.9 percent weight/volume lactic acid, sufficient sodium hydroxide to afford a pH of about 4.0, about 20 percent weight/volume propylene glycol and sufficient water for injection to afford an aqueous solution containing the recited ingredient concentration.

TABLE I

Unacceptable Formulations-% (wt/vol)

| Active Ingredient | | | | | | | |
|---|---|---|---|---|---|---|---|
| Ciramadol.HCl | 6.0 | 6.0 | 6.0 | 6.0 | 6.0 | 6.0 | 6.0 |
| Antioxidants | | | | | | | |
| Disodium EDTA | 0.1 | — | 0.1 | — | — | — | — |
| Na Bisulfite | 0.1 | 0.1 | 0.2 | — | — | — | — |
| Monothioglycerol | — | — | 0.2 | 0.5 | 0.5 | — | — |
| Cysteine.HCl | — | — | — | — | — | 0.1 | — |
| Preservatives | | | | | | | |
| Benzethonium chloride | — | — | — | 0.01 | 0.01 | — | — |
| Phenol | 0.5 | 0.5 | — | — | — | — | — |
| Benzyl Alcohol | — | — | 0.9 | — | — | — | — |
| Buffers | | | | | | | |
| Na Acetate | 0.47 | — | — | 0.47 | — | — | — |
| Acetic Acid | q.s. pH 4.5 | — | — | q.s. pH 4.5 | — | — | — |
| Na Citrate | — | 0.18 | — | — | — | — | — |
| Citric Acid | — | 0.23 | — | — | — | — | — |
| Monobasic Na Phosphate | — | — | 1.2 | — | — | — | — |
| Phosphoric Acid (conc.) | — | — | q.s. pH 4.5 | — | — | — | — |
| Na Tartrate | — | — | — | — | 1.7 | 1.7 | 1.7 |
| Tartaric Acid | — | — | — | — | 0.37 | 0.37 | 0.37 |
| NaOH | — | q.s. pH 4.5 | — | — | q.s. pH 4.0 | q.s. pH 4.0 | q.s. pH 4.0 |
| Diluent | | | | | | | |
| H₂O | qs | qs | qs | qs | qs | qs | qs |

TABLE II

Acceptable Formulations-% (wt/vol)

| | | | | | |
|---|---|---|---|---|---|
| Ciramadol.HCl | 6.0 | 6.0 | 6.0 | 6.0 | 6.0 |
| Sodium Bisulfite | — | — | — | 0.5 | — |
| Monothioglycerol | 0.5 | 0.5 | 0.5 | — | 0.5 |
| Benzethonium Chloride | 0.01 | — | 0.01 | 0.01 | — |
| Sodium Tartrate | — | 1.7 | 1.7 | 1.7 | — |
| Tartaric Acid | — | 0.37 | 0.37 | 0.37 | — |
| Lactic Acid | 0.9 | — | — | — | 0.9 |
| NaOH | q.s. pH 4.5 | q.s. pH 4.5 | q.s. pH 4.5 | q.s. pH 4.0 | q.s. pH 4.0 |
| Propylene Glycol | 21 | 21 | 21 | 21 | 21 |
| H₂O | qs | qs | qs | qs | qs |

What is claimed is:

1. A parenterally acceptable, aqueous composition comprising from 0.05 to about 0.5 percent weight/volume of an antioxidant selected from the group consisting of monothioglycerol (NF), sodium bisulfite, sodium bisulfite and disodium ethylenediamine-tetraacetic acid, and disodium ethylenediamine-tetraacetic acid and monothioglycerol (NF); from 0.5 to about 2.0 percent weight/volume of a buffer selected from the group consisting of lactate, tartrate, citrate and acetate buffer systems, to afford a pH of from about 3 to about 4.5; from 0 to about 0.01 percent weight/volume of benzethonium chloride; from about 20 to about 40 percent weight/volume of propylene glycol (USP); and from about 1.0 to about 10.0 percent weight/volume of a pharmaceutically acceptable acid addition salt of 1-cis-2(α-dimethylamino-m-hydroxybenzyl)-cyclohexanol.

2. A composition of claim 1 which comprises about 1.0 to about 6.0 percent weight/volume of 1-cis-2(α-

4. A composition of claim 1 which comprises 3.0 percent weight/volume 1-cis-2(α-dimethylamino-m-hydroxybenzyl)cyclohexanol·HCl, about 0.5 percent weight/volume monothioglycerol, about 0.9 percent weight/volume lactic acid, sufficient sodium hydroxide to afford a pH of about 4.0, about 20 percent weight/volume propylene glycol and sufficient water for injection to afford an aqueous solution containing the recited ingredient concentration.

5. A composition of claim 1 which comprises 6.0 percent weight/volume 1-cis-2(α-dimethylamino-m-hydroxybenzyl)cyclohexanol·HCl, about 0.5 percent weight/volume monothioglycerol, about 0.9 percent weight/volume lactic acid, sufficient sodium hydroxide to afford a pH of about 4.0, about 20 percent weight/volume propylene glycol and sufficient water for injection to afford an aqueous solution containing the recited ingredient concentration.

* * * * *